United States Patent [19]
Eggleston et al.

[11] Patent Number: 5,720,744
[45] Date of Patent: Feb. 24, 1998

[54] CONTROL SYSTEM FOR NEUROSURGERY

[75] Inventors: Jeffrey L. Eggleston, Broomfield; James H. Orszulak, Nederland; Matthew J. Sodnicar, Lafayette, all of Colo.

[73] Assignee: Valleylab Inc, Boulder, Colo.

[21] Appl. No.: 470,533

[22] Filed: Jun. 6, 1995

[51] Int. Cl.$^6$ ........................................ A61B 17/39
[52] U.S. Cl. .................................. 606/40; 606/38
[58] Field of Search .......................... 606/34, 38, 40, 606/50, 51

[56] References Cited

U.S. PATENT DOCUMENTS

| | | |
|---|---|---|
| 4,041,952 | 8/1977 | Morrison, Jr. et al. |
| 4,474,179 | 10/1984 | Koch. |
| 4,492,231 | 1/1985 | Auth. |
| 4,520,818 | 6/1985 | Mickiewicz .................. 606/40 |
| 4,590,934 | 5/1986 | Malis et al. |
| 4,658,819 | 4/1987 | Harris et al. |
| 4,890,610 | 1/1990 | Kirwan, Sr. et al. |
| 4,969,885 | 11/1990 | Farin. |
| 5,196,009 | 3/1993 | Kirwan, Jr. |
| 5,318,563 | 6/1994 | Malis et al. |
| 5,422,567 | 6/1995 | Matsunaga .................. 606/40 |
| 5,443,463 | 8/1995 | Stern et al. .................. 606/51 |
| 5,514,129 | 5/1996 | Smith .......................... 606/40 |

FOREIGN PATENT DOCUMENTS

| | | | |
|---|---|---|---|
| 3904558 | 8/1990 | Germany ..................... | 606/40 |

OTHER PUBLICATIONS

Article: Automatically controlled bipolar electrocoagulation—"COA–COMP".
Article: Studies on coagulation and the development of an automatic computerized bipolar coagulator.

*Primary Examiner*—Lee S. Cohen
*Attorney, Agent, or Firm*—Peter C. Richardson; Lawrence C. Akers; Aaron Passman

[57] ABSTRACT

A control system and method for the operation of neurosurgical bipolar electrodes for application to the tissue and bodily fluids of a patient provides a source of high frequency energy connected to bipolar electrodes. Contacting surfaces are on the bipolar electrodes of highly electrically conductive material with resistance per unit area substantially less than the impedance of the tissue and bodily fluids. A current transducer attached to the source of high frequency energy responds to the RMS current applied through the tissue and bodily fluids between the contact surfaces as a measure relative to the instantaneous values of the RMS current. A current transducer attached to the source of high frequency energy responds to the RMS current through a capacitor applied across the contact surfaces to provide a signal correlated to the instantaneous values of the RMS voltage between the contacts and across the tissue and bodily fluids. A control connects to the source of high frequency energy for initially regulating the RMS current applied through the tissue and bodily fluids by the contacting surfaces in response to the impedance until the signal divided by the measure reaches a predetermined value. The control regulates the RMS power applied to the tissue and bodily fluids by the contacting surfaces in accord with the impedance until the signal divided by the measure reaches a predefined value. The control responds to the measure and the signal so that the RMS voltage applied to the impedance being treated between the contacting surfaces is regulated while monitored until a prescribed value is reached. The control regulates the RMS voltage applied to the tissue and bodily fluids by the contacting surfaces in accord with the impedance by changing the RMS voltage to a percentage of that applied until the prescribed value is obtained so that the tissue and bodily fluids being treated are moist but coagulated at the surface and not completely dry and carbonized or turned to eschar.

15 Claims, 6 Drawing Sheets

CONTROL SYSTEM FOR NEUROSURGERY

Related applications incorporated herein and made a part hereof by reference and filed on the same date as this application:

Power Control for An Electrosurgical Generator; U.S. Ser. No. 08/471,116; PC8826; now abandoned;

Digital Waveform Generation for Electrosurgical Generators; U.S. Ser. No. 08/471,344; PC9210;

Control Apparatus for Electrosurgical Generator Power Output; U.S. Ser. No. 08/468,950; PC8827; now U.S. Pat. No. 5,599,344;

Exit Spark Control for an Electrosurgical Generator; U.S. Ser. No. 08/479,424; PC9217; now U.S. Pat. No. 5,628,745.

1. FIELD OF THE INVENTION

A control system for neurosurgical bipolar electrodes for application by a surgeon to and bodily fluids of a patient and more particularly the control system regulates the RMS current, RMS power and RMS voltage applied to the tissue and bodily fluids by the contacting surfaces in accord with the impedance in the tissue and bodily fluid.

2. BACKGROUND OF THE INVENTION

Neurological electrosurgery has been performed by low power electrosurgical energy application on an operative site flooded with a conductive medium such as saline or Ringer's solution in an effort to prevent over-cauterizing the tissue or bodily fluids and forming eschar that sticks to the treating instrument. The problem with this approach to prevent the formation of eschar that sticks to the instrument is that the flooded operative site obscures the precise area of the surgery. Moreover the saline while keeping the tissue treated moist also heats and spreads the area of tissue treatment beyond that desired.

U.S. Pat. No. 4,590,934 has a system with low output impedance to maintain uniform power at the bipolar tips of the forceps over a wide range of load conditions from dry to heavily irrigated tissue. A stiffly regulated isolated power output having an output impedance of 5 to 10 ohms is in '934 as contrasted with the previous solid state systems of 50 to 500 ohm and the spark gap (Bovie) with 40 to 50 ohms. Consequently, the lower impedance output of '934 can be used under constant irrigation for cooling and protecting adjacent delicate vessel, nerve and tissue structures.

U.S. Pat. No. 5,318,563 has a bipolar electrode supplied with an aperiodic sequence of uniform width bursts of high frequency signal with a substantially identical decaying amplitude envelopes on the bursts so each envelope has a predetermined rate of change from preselected initial amplitude. The '563 generator operates in cut and coagulation modes and has a variable direct current voltage power supply, a short and open circuit detectors for the bipolar electrodes.

U.S. Pat. No. 4,041,952 has a switch on a forceps that can be used as monopolar or bipolar as needed by the surgeon during treatment of the patient with electrosurgery. U.S. Pat. No. 4,890,610 has a pair of bipolar forceps composed of coined metallic conductive blades that are each overmolded with a plastic insulator to leave exposed tips at the patient end and connector terminals for electrosurgical energy at the opposite ends. U.S. Pat. No. 4,492,231 has a bipolar circuit to provide non stick coagulation therebetween by use of a good thermal conductor and minimal contact relative to the volume of material in the tines of the forceps. U.S. Pat. No. 5,196,009 has a non-sticking set of bipolar forceps made by coining the first and second blade portions of nickel with large thermal conductivity. U.S. Pat. No. 4,969,885 recognizes the merit is controlling the output voltage rather than the output power in a high frequency generator by an automatic regulation loop. An output voltage rather than power is used to control the electrosurgical cutting or coagulation via an automatic regulation loop. Thus the voltage control in '885 is acknowledged to represent a way to control the degree of thermal damage and conversely automatically monitoring the delivered power is said to be nonexistent. Specifically, the delivered by an electrosurgical device and the power required for electrosurgery at any moment is never constant so reproducibility for cutting or coagulation of tissue is inconsistent. Optimal power generation and delivery by an electrosurgical device can not be obtained and so automatic monitoring of control power is impossible in high frequency surgical devices.

The output voltage control of '885 is limited to voltage control when the voltage is constant during electrosurgery. Since the output voltage is regulated and controlled to an adjustable signal reference source, crest factor changes to that output would invalidate regulation control resulting in a loss of the quality of tissue effect achieved during cutting or coagulation by electrosurgery. The overall quality is limited to the correlation of the signal reference source to the particular tissue characteristics. The dynamics of the tissue changes are thus unaddressable.

U.S. Pat. No. 4,474,179 has low power coagulation control circuit for a bipolar surgical instrument responsive to the differential quotient of the impedance, i.e. the change of impedance with respect to time at the tissue treated. Specifically, the impedance change is measured with respect to time and either the power or the time duration of the application is controlled. U.S. Pat. No. 4,658,819 discloses a power curve for control of the application of electrosurgical power to a bipolar instrument. Significant to the '819 teaching is the initial constant current application of energy, then the constant power application of energy and finally the decrease of the power output in accord with the square of the impedance. Notable is the lack of any appreciation of the control of the application of energy as a function of identified impedance values after applying a source of constant current, then after applying a source of constant power and finally after applying a factored source of constant voltage.

Disclosed hereinafter will be a solution to the limitations of the mentioned patents. In particular the neurosurgical bipolar electrode and electrosurgical generator described and illustrated performs neurosurgery with a control to regulate in real time the applied power as a function of the tissue dynamic impedance. A closed loop control has real time dynamic tissue impedance monitoring providing minimal sticking, charring and excellent coagulation. The mentioned prior patents are incorporated herein by reference and made a part hereof.

SUMMARY OF THE INVENTION

A control system for neurosurgical bipolar electrodes for application by a surgeon to the tissue and bodily fluids a patient preferably has a source of high frequency energy in the form of an electrosurgical generator. Bipolar electrodes may connect to the source of high frequency energy. Tissue and bodily fluid contacting surfaces on the bipolar electrodes are most preferably of highly electrically conductive material with resistance per unit area substantially less than the impedance of the tissue and bodily fluids. A first current transducer inductively attached to the connection between the source of high frequency energy and one of the contact surfaces may respond to the instantaneously varying impedance of the load of the tissue and bodily fluids at the particular instant of treatment of the tissue and bodily fluids. The first current transducer provides a measure relative to the instantaneous values of the RMS between the contact surfaces and through the tissue and bodily fluids.

A second current transducer attached to the source of high frequency energy responds to the RMS current through a capacitor applied across the contact surfaces. The second current transducer provides a signal of the varying current changes due to the tissue impedance load on the source of high frequency energy and changes in the output thereof due to variance in the radio frequency sourced energy, the second current transducer providing the signal representative of and correlated to by a weighted value to the instantaneous value of RMS voltage across the tissue and bodily fluids between the contact surfaces.

A control connected to the source of high frequency energy for initially regulating the RMS current applied through the tissue and bodily fluids by the contacting surfaces most preferably responds to the impedance therethrough until the signal divided by the measure is a predetermined value. The control may then connect for regulating the RMS power applied to the tissue and bodily fluids by the contacting surfaces in accord with the impedance in the tissue and bodily fluid until the signal divided by the measure is a predefined value. The control thereafter might respond to the signal divided by the measure so that the RMS voltage applied to the impedance of the tissue and bodily fluids being treated between the contacting surfaces is regulated while monitored until the signal divided by the measure is a prescribed value. The control may connect for finally regulating the RMS voltage applied to the tissue and bodily fluids by the contacting surfaces in accord with the impedance in the tissue by changing the RMS voltage to a percentage of that applied to the tissue and bodily fluid until the prescribed value is obtained so that the tissue and bodily fluids being treated are preferably moist but coagulated at the surface and not completely dry and carbonized or turned to eschar.

The control might include the microprocessor preferably operates in the binary system. The microprocessor divides the signal by the measure. The microprocessor might have memory for the predetermined value, the predefined value and the prescribed value and the microprocessor compares the predetermined value, the predefined value and the prescribed value to the signal divided by the measure in real time. The controllably maintains the RMS current substantially constant until the signal divided by the measure is the predetermined value of sixteen. The control preferably maintains the RMS power substantially constant until the signal divided by the measure is the predefined value of five hundred and twelve. The control then preferably maintains the RMS voltage substantially regulated until the signal divided by the measure is the prescribed value of one thousand and twenty four. The control preferably maintains the RMS voltage at a percentage of its substantially regulated level after the signal divided by the measure is the prescribed value of one thousand and twenty four. The RMS signal and RMS measure may be multiplied in the microprocessor to calculate RMS power in real time. The source of high frequency energy may be limited to a range of between about 1 and 70 watts of output. The contact surfaces could be a noble metal, nickel or alloys thereof selected for their electrically and thermally conductive characteristics. A switch, preferably foot operated, controls the source of high frequency energy to the bipolar electrodes as the surgeon activates and makes the connection therebetween. The control preferably maintains the RMS voltage at one hundred percent of its substantially regulated level after the signal divided by the measure is the prescribed value of one thousand and twenty four. Alternatively, the control may maintain the RMS voltage at a percentage of one hundred percent of its substantially regulated level, e.g. fifty percent after the signal divided by the measure is the prescribed value of one thousand and twenty four.

A method for controlling a system for neurosurgical bipolar electrodes for application to the tissue and bodily fluids of a patient may have steps including providing a source of high frequency energy and connecting bipolar electrodes to the source of high frequency energy. Providing contacting surfaces on the bipolar electrodes and contacting the tissue and bodily fluids with the contacting surfaces of highly electrically conductive material with resistance per unit area substantially less than the impedance of the tissue and bodily fluids are also steps. Having a tank network in the source of high frequency energy that includes capacitors and inductors tuned to the operating frequency of the source of high frequency energy in the tank network is another step. A step of providing an output of the source of high frequency energy as the tank network may be a part of the method. Inductive attaching a first current transducer to the connection between the source of high frequency energy and one of the contact surfaces might be a step. The steps of responding with the first current transducer to the instantaneously varying impedance of the load of the tissue and bodily fluids at the particular instant of treatment of the tissue and bodily fluids and providing with the first current transducer a measure relative to the instantaneous values of the RMS current between the contact surfaces and through the tissue and bodily fluids can be followed. Responding to the RMS current applied through the tissue and bodily fluids between the contact surfaces is a step. Inductively attaching a second current transducer to the source of high frequency energy to respond to the RMS current through a capacitor applied across the contact surfaces could be a step. Providing with the second current transducer the signal of the varying current changes due to the tissue impedance load on the source of high frequency energy and changes in the output thereof due to variance in the radio frequency sourced energy may be a step of the method. The step of providing with the second current transducer the signal representative of the instantaneous value of RMS voltage across the tissue and bodily fluids between the contact surfaces is followed in the method. Providing with the second transducer the signal correlated to by a weighted value of the instantaneous value of RMS voltage can be a method step. The steps of connecting a control to the source of high frequency energy for initially regulating the RMS current applied through the tissue and bodily fluids by the contacting surfaces and responding with the control to the impedance the tissue and bodily fluids until the signal divided by the measure reaches a predetermined value may be added steps. Connecting the control for then regulating the RMS power applied to the tissue and bodily fluids by the contacting surfaces in accord with the impedance in the tissue and bodily fluid until the signal divided by the measure reaches a predefined value might be a step. Responding thereafter with the control to the signal divided by the measure so that the RMS voltage applied to the impedance of the tissue and bodily fluids being treated between the contacting surfaces is regulated while monitored until the signal divided by the measure of a prescribed value, the control connected for finally regulating the RMS voltage applied to the tissue and bodily fluids by the contacting surfaces in accord with the impedance in the tissue by changing the RMS voltage to a percentage of that applied to the tissue and bodily fluid until the prescribed value is obtained so that the tissue and bodily fluids being treated are moist but coagulated at the surface and not completely dry and carbonized or turned to eschar is yet a further step of the method.

DETAILED DESCRIPTION OF THE INVENTION

Figure 1:
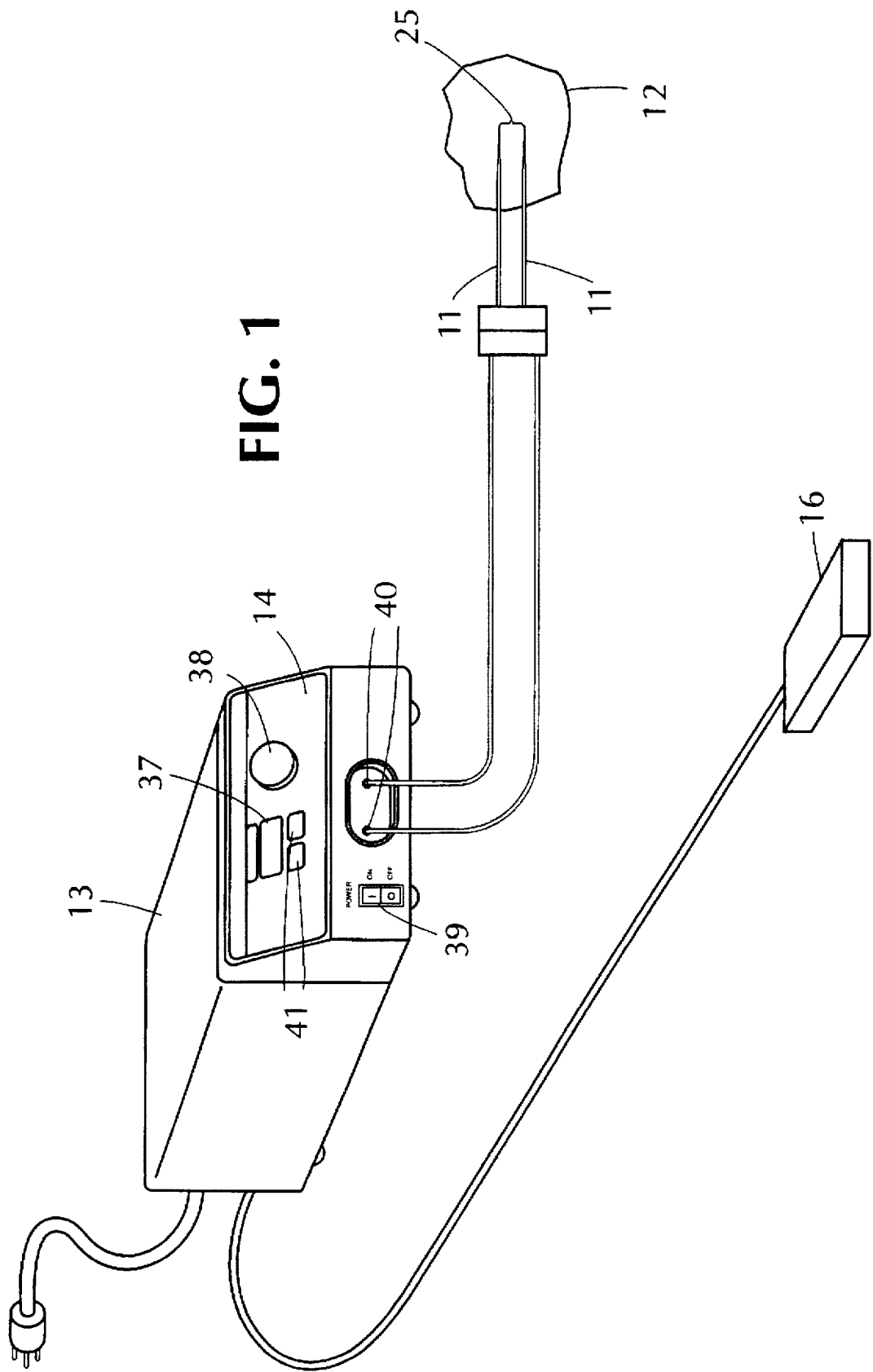
FIG. 1 is a schematic representation of the neurosurgical bipolar control system with the relationships of the components shown as they would appear to a surgeon.
Figure 2:
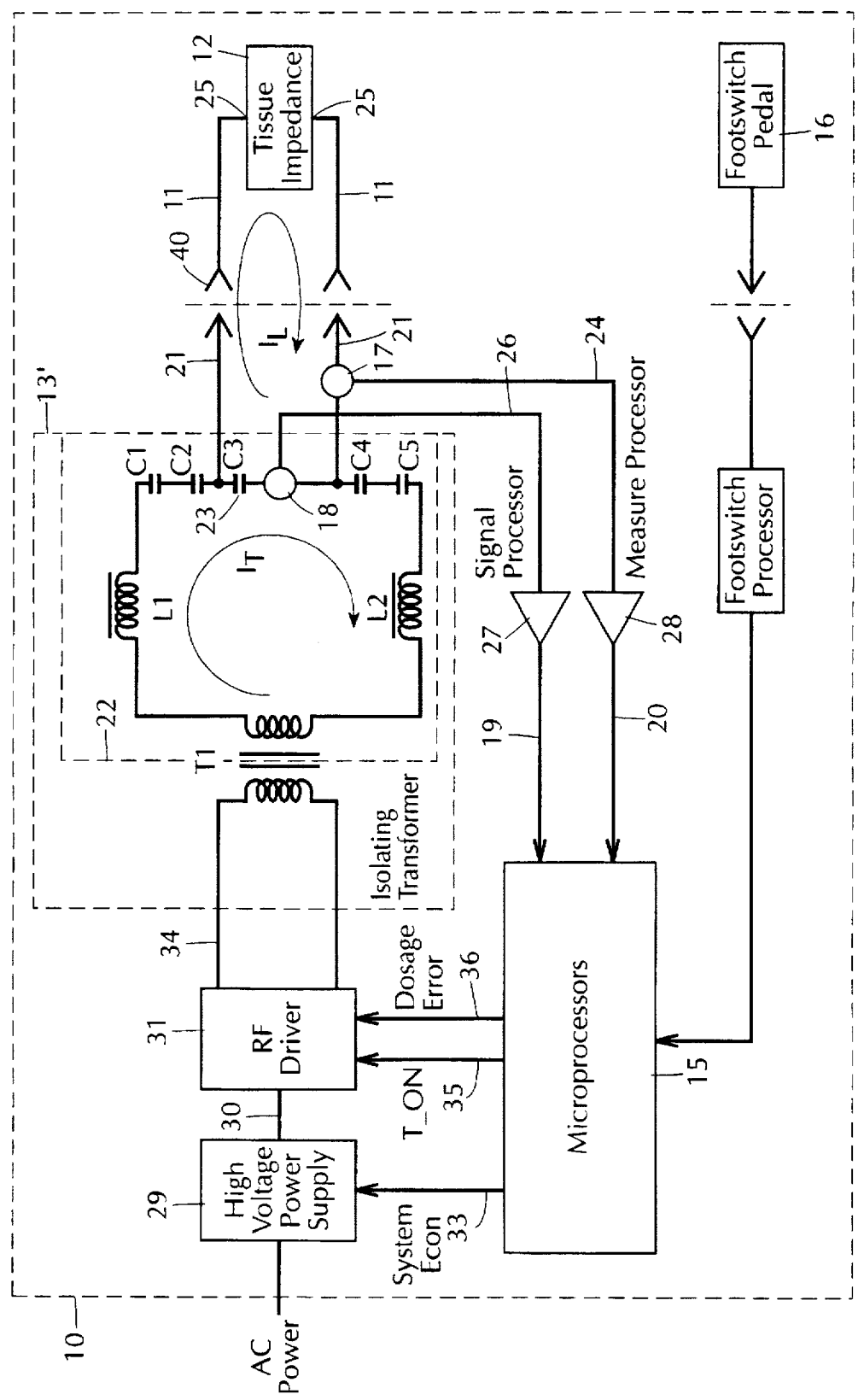
FIG. 2 is a schematic circuit diagram of the tank network and the neurosurgical control system of FIG. 1.
Figure 3:
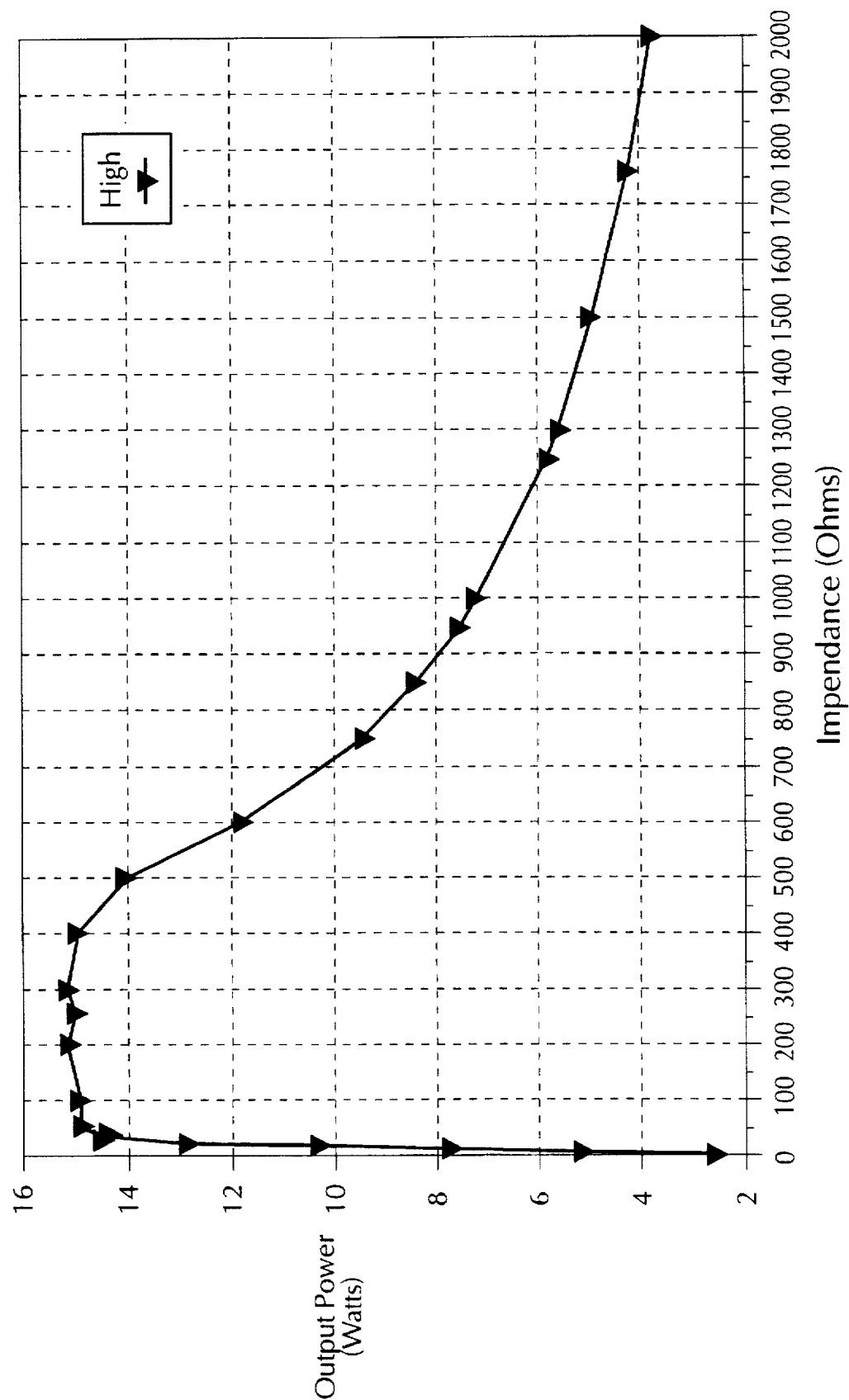
FIG. 3 is a plot of the preferred power curve automatically generated by the control system after initiation of the foot switch.
Figure 4:
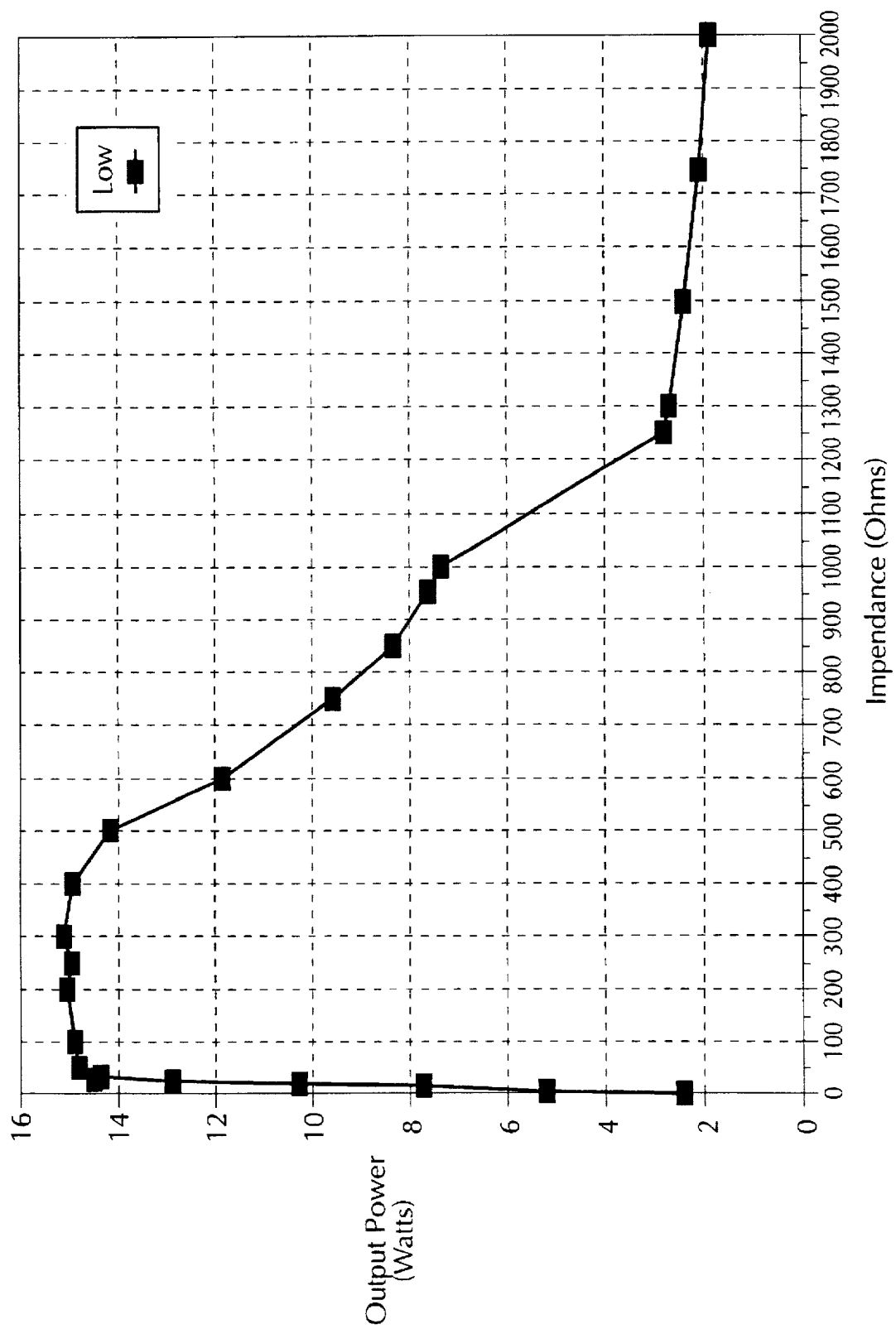
FIG. 4 is a plot of an alternate power curve automatically generated by the control system after initiation of the foot switch and in particular the regulated voltage decrease by a percentage after a specific impedance is reached.

A control system 10 as shown schematically in FIG. 2 for neurosurgical bipolar electrodes 11 for application by a surgeon to the tissue and bodily fluids 12 of a patient has a source of high frequency energy 13' preferably in the form of an electrosurgical generator 13 that is settable to a desired power on a front panel 14 thereof by an operating nurse under the supervision and instructions of a brain surgeon. Ordinarily the power level selected will be less than fifteen watts on a Valleylab NS 2000 neurosurgical generator, as shown in FIG. 1. This instrument, has a microprocessor 15 therein, that calculates the desired current as the square root of the number of the selected power level divided by sixteen. The desired current is thereby calculated for the initial resistance of tissue and bodily fluid impedance between zero and sixteen ohms. Full desired voltage across the tissue and bodily fluids 12 impedance or load of five hundred and twelve ohms is the square root of the number of the desired power selected, as set on the front panel 14, multiplied by the impedance of five hundred and twelve, see FIG. 3 for a plot of the power curve described. One half the desired voltage is the square root of the number of the desired power selected multiplied by one thousand twenty four which is then divided by two, as illustrated in FIG. 4. The foregoing calculations are made after the desired power has been selected and when a foot switch 16 is depressed to activate the source of high frequency energy 13'. The control system 10 is largely automatic and responsive to the surgeon's application of the bipolar electrodes 11 to the patient's tissue and bodily fluids 12. The contact with the patient's tissue will initially, after keying, deliver actual power to the tissue while the impedance of that load is monitored. In real time the calculations of actual power are continually performed by multiplying the root mean square found for the tissue and bodily fluids 12 using a first current transducer 17 and a second current transducer 18.

First and second current transducers 17 and 18 pick up current flow, as shown in FIG. 2, and monitor the dynamic tissue impedance during the electrosurgical treatment of tissue or bodily fluids 12 for correlating the signal and measure values 19 and 20 to the tissue voltage and current.

The first current transducer 17 monitors the current $I_L$ flowing in a lead 21 of the bipolar forceps 11, that current $I_L$ flow is responsive to the instantaneously varying impedance of the load of the tissue and bodily fluids 12 being treated at the particular instant that the monitoring is taken. Similarly, the second current transducer 18 is located in the source of high frequency energy 13' having a tank network 22 shown therein, in FIG. 2. The second current transducer 18 monitors the varying current $I_T$ changes due to the tissue impedance load on the source of high frequency energy 13' and changes in the output thereof because of a variance in the radio frequency sourced energy. The second current transducer 18 is attached to the source of high frequency energy 13' to respond to the RMS currents $I_L$ and $I_T$ through a capacitor 23 applied across contact surfaces 25, shown in FIG. 2. This second current transducer 18 can provide the signal 26 correlated to the instantaneous value of RMS voltage across the tissue and bodily fluids 12 between the contact surfaces 25, as will be discussed in detail. The current sensed by this second current transducer 18 correlates by means of a weighted value responsive to the RMS currents $I_L$ and $I_T$ through the capacitor 23 that is applied across the contact surfaces 25. The instantaneous monitoring of those currents $I_L$ and $I_T$ are further used to evaluate the power required and instruct the control system 10 for proper operation in response to the desiccation of the tissue and bodily fluids 12 being treated.

These monitored currents $I_L$ and $I_T$ when processed by signal and measured processor circuits 27 and 28 become the signal and measure values 19 and 20 used in the microprocessor 15 to calculate the actual power in the load. The actual power is found continually after the electrosurgical generator or source of high frequency energy 13' is keyed. In particular, several hundred times per second so that real time monitoring is performed.

FIG. 2 is the schematic circuit diagram of the tank network 22 and the control system 10. Hardware and software control processing in control system 10 yields the desired dynamic impedance response with the surgical result identified wherein minimal charring and improved coagulative hemostasis is obtained. Closed loop controlled application of energy is provided by the control system 10 of FIG. 2 using real time tissue impedance monitoring to regulate instantaneously the energy delivered.

In the electrosurgical generator 13, a high voltage power supply 29 provides a regulated output voltage 30 to a Rf driver 31 by means of AC to DC power conversion using a pulse width modulated control, an inherent property of the high voltage power supply 29. The regulated output voltage 30 from the high voltage power supply 29 is further controlled by a system ECON 33, which is a DC voltage level generated by the microprocessor 15 as a function of the processed signal 19 and measure 20 values correlated to the tissue voltage and current determined by the real time tissue impedance dynamic changes.

The radio frequency driver 31 in the electrosurgical generator 13 provides a regulated source of radio frequency energy 34 to the tank network 22 of the electrosurgical generator 13 which preferably operates at a frequency of approximately 473 kHz. The output 34 of the radio frequency driver 31 has a quasi resonant topology to provide a regulated pulsed voltage whose frequency is controlled by the T ON 35, drive gating signal, as shown in FIG. 2, generated by the microprocessor 15. This T ON waveform actively enabled by the microprocessor 15 after the foot switch 16 is pressed initiates activation of the radio frequency bipolar electrosurgical output energy 21 to the bipolar forceps 11. The radio frequency driver 31 pulsed amplitude is tightly regulated and controlled through the regulated output 30 of the high voltage power supply 29 which is provided as input to the radio frequency driver 31. The pulse width is controlled to an approximate fifty percent duty and is governed by the in-circuit tuning of components in the radio frequency driver 31 and tank network 22. Through the use of the microprocessor 15 and the tissue correlated voltage and current as represented by the signal 19 and measure 20 values, continuous monitoring of the developed energy of the radio frequency driver 31 is performed by a dosage error inhibit command 36. In the event that the power generated by the electrosurgical generator 13 shown in FIG. 1, becomes excessive, i.e. over and above the desired, delivered power plus margin as shown by a power display 37 in accord with the setting of a knob 38, the dosage error command disables the radio frequency driver 31 operation and safely shuts down the electrosurgical generator 13 system. Active dosage error monitoring is provided for every setting of the knob 38. With evidence of any appropriate software error code on the display 37, the electrosurgical generator 13 returns to proper operation with the power cycling of the AC power switch 39 on the front panel 14, seen in FIG. 1.

The tank network 22, in FIG. 2, generates radio frequency energy 21 as the output of the source of high frequency energy 13' of the electrosurgical generator 13 for the bipolar forceps 11. Inductive and capacitive components, L1, L2 and C1 through C5 are in the tank network 22 to provide wave shape tuning and filtering of the pulsed voltage 34, received as input from the RF driver 31. Isolation transformer T1, isolates and safely transfers the radio frequency energy 21 to the patient via the bipolar forceps 11, minimizing leakage and hazard during neurosurgery. Wave shape tuning and filtering performed in the tank network 22 converts the pulsed voltage 34 from the RF driver 31 to a continuous sinusoidal wave at the bipolar output, shown as a pair of jacks 40. The inductive quality of the filtering provided by isolation transformer T1 has leakage inductance combined with chokes L1 and L2 connected in series. Capacitors C1 through C5 located in the tank network 22 includes C3 which is capacitor 23 to provide the final filtering and attenuation of the developed sourcing power 21.

In addition to providing the wave shape smoothing or filtering quality of the inductive and capacitive components, the tank network 22 resonant current automatically controls the developed and delivered output power 21 with a high degree of precision. This is accomplished through the use of non contacting first and second current transducers 17 and 18, shown in FIG. 2. Second current transducer 18 bidirectionally monitors the radio frequency sourcing energy 21 by measuring changes to the tank network 22 current $I_T$. In addition, $I_T$ is also an indicator of the load current, $I_L$, in real time, that is, the variance of the dynamic tissue impedance occurring during neurosurgery.

Significant advantages over merely monitoring voltage are realized with the first and second current transducers 17 and 18, in the closed loop control system 10 as described and shown in FIG. 2. Real time high precision power delivery using closed loop control system 10 is possible due to the inherently fast response of the described first and second current transducers 17 and 18 over voltage transformer coupled monitoring systems as in the prior '885 patent. First and second current transducers 17 and 18 exhibit a wide bandwidth response due to their low impedance characteristic. The operating self resonance of the first and second current transducers 17 and 18 is higher than transformer coupled voltage monitoring, providing the benefit of wide dynamic range and linearized control of radio frequency power 21 delivered to tissue and bodily fluids 12 during electrosurgery. Increased precision with the radio frequency power control system 10 is thus provided because of the self resonance property of the applied current monitoring first and second current transducers 17 and 18. Thus, parasitic losses are lower, resulting in lower quantization losses and therefore increases monitoring accuracy. Voltage transformers, are higher impedance sensing devices than the first and second current transducers 17 and 18 because the voltage transformers exhibit lower self resonance parameters contributing to higher losses and increased error to any monitoring particularly as the frequency of operation increases.

Since electrosurgery is performed at high RF operating frequencies to avoid muscular stimulation, errors with voltage transformer coupled monitoring systems will be present and contribute to decreased accuracy and control. In neurosurgical use, voltage monitoring will have lower control response to dynamic impedance changes of the treated tissue adversely impacting the quality of the surgical result, increasing charring and tissue sticking or inadequate coagulation.

Non contact monitoring enabled by the tank network 22 of FIG. 2, increases monitoring precision and control and increases quality tissue treatment by eliminating high frequency reflective losses as present with hardwired voltage transformer monitoring which is a dynamic parallel shunt of the tissue load or impedance. During surgery, this loss in impedance monitoring results in a less accurate tissue response and therefore less control.

Second current transducer 18 monitors $I_T$ and $I_L$ providing a significant advantage in the operation of the neurosurgical bipolar control system 10 shown in FIG. 2. Specifically and unlike prior voltage control systems using transformer coupled signal monitoring that provide scaler voltage quantities of the applied Vrms to the tissue, the second current transducer 18 monitors current flow, automatically giving a time dependent correlation weighted value of the tissue root mean square voltage, a time variant as a function of the applied power. This weighted value designated as the signal 19 representing tissue correlated voltage, is important to the monitoring of dynamic impedance in real time. Consequently, the weighted value of the signal 19 and the measure 20 are used to correlate to the time dependent relationship of the dynamic tissue impedance changes during surgery.

This preferred result is achieved by not measuring the scalar magnitude constant of the Vrms output voltage present at the bipolar forceps 11, but rather by measuring current $I_T$ in the tank network 22 as a consequence of the dynamic load. More specifically, using the mathematical current to voltage relationship, hereinafter derived, and processing provided by capacitor 23 also known as C3. Second current transducer 18 located in series with capacitor 23 and not across the output of the electrosurgical generator 13 by monitoring current flow and not voltage provides a representation of the time rate of change of the bipolar forceps 11 contact surfaces 25 root mean square voltage during application of power. The current to voltage relationship of C3 capacitor 23 is provided by the following equation (2).

In FIG. 2, the tissue rms voltage=Voltage across component C3=V(C3) and;

$$V(C3)=1/C3 \ \{\text{the integral from 0 to t of } (i_T-i_L) \ dt\} \qquad (1)$$

where; t=time dependent variable with the application of power to the tissue;

and; $(i_T-i_L)$=instantaneous current by the second current transducer 18 then; differentiating equation (1), yields $$(i_T-i_L)=C3 \ dV(C3)/dt \qquad (2).$$

The signal processor amplifier 27 and the monitor processor amplifier 28 of FIG. 2 use the transducer currents 24 and 26 monitored by first and second current transducers 17 and 18. These amplifiers 27 and 28 provide a precise level of absolute value signal conversion to generate the signal 19 and the measure 20 used in the microprocessor 15 to calculate the actual power 21 in the load.

The microprocessor 15 calculates in accord with its programming the control system 10 ECON 33 value which modifies the high voltage power supply 29 output 30 and in turn modifies the RF power from the electrosurgical generator 13 as output to the tissue and bodily fluids 12 in the closed loop of FIG. 2. Upon active keying of the electrosurgical generator 13 to produce an RF output, i.e. applied power, the signal 19 is digitized in the microprocessor 15 instantaneously and multiplied by a scale factor to make it VSCALED. Similarly, the measure 20 is digitized in the microprocessor 15 instantaneously and multiplied by the same scale factor to generate ISCALED. When multiplied together, a scaled number of the instantaneous actual power is determined by the microprocessor 15 and applied as ECON 33.

Active keying of the electrosurgical generator 13 is accomplished by pressure on the foot switch 16 to generate an optically coupled enable request to the microprocessor 15. Once received by the microprocessor 15, the T ON gating pulse is generated to trigger the RF driver 31 to develop the prescribed pulsed voltage level 34 for setting the RF or electrosurgical generator 13 source of high frequency energy 13' output power level 21 delivered to the tissue and bodily fluids 12, as shown in FIG. 2.

This is not all that has to be done after initial keying to operate the control system 10. FIGS. 3 and 4 are typical power curves wherein the vertical scale is in watts and the horizontal is impedance. The power applied to the tissue must be regulated so that the tissue and bodily fluids 12 are coagulated but do not stick to the bipolar forceps 11. The power curves shown in FIGS. 3 and 4 automatically control the power supplied to coagulate after the surgeon has placed the bipolar forceps 11 against the tissue and bodily fluids 12 and pressed the foot switch 16 to key the source of high frequency energy 13'. That is to say that the operation thereafter is controlled according to the power curve in FIGS. 3 and 4.

Note that there are essentially four areas of each power curve of FIGS. 3 and 4 which can be designated initiation, desiccation, high coagulation and low coagulation. The four areas are associated with impedance ranges as described and as determined during the automatic operation of the control system 10. The heat generated by the passage of high frequency electrosurgery between the bipolar forceps 11 and across the tissue and bodily fluids 12 during the desiccation must be controlled so as to be enough to dry out the operative site but not cook the tissue and bodily fluids 12 to the bipolar forceps 11. To that end the control system 10 applies the power in a particular fashion which is selected to initiate the power flow with relatively high current at the control front panel 14 power as set by the knob 38.

The software in the microprocessor 15 is programmed to find after keying if Iscaled is greater than 64 times the number for Vscaled then the impedance must be less than sixteen ohms. The output of the microprocessor 15 is called system Econ 33 as voltage control, a feedback technique programmed into the microprocessor 15 to manage the output 21 of the source of high frequency energy 13'. The management scheme is simply that Econ 33 is plus one or minus one to increase the output 21 or decrease the output 21 according to the perceived needs as figured by the software.

If Iscaled is more than twice Vscaled then the impedance must be greater than sixteen ohms and less than five hundred and twelve. The feedback technique programmed into as an instruction is three which to the microprocessor 15 software keeps the power essentially substantially constant as per the dithering of the Econ 33 to plus or minus one. The substantially constant power application of the high frequency energy desiccates the tissue and bodily fluids 12 until nearly dry as evidenced by the rise in the impedance from sixteen to five hundred and twelve ohms.

If Iscaled is greater than Vscaled and the impedance is greater than five hundred and twelve ohms but less than one thousand and twenty four the desired voltage is one hundred percent of the level calculated by multiplying the front panel 14 power by five hundred and twelve and taking the square root of that value. From FIG. 3 a plot of power against impedance the power curve is rolled off per the desired levels. The decrease in power evidenced in the plot is sufficient to lower the energy from the source of high frequency energy 13' enough to diminish the rate of desiccation of tissue and bodily fluids 12, if any, between the bipolar forceps 11 and thereby prevent the coagulation or sticking to the tips or contact surfaces 25 thereof.

It is desirable that, the automatic power regulation of the control system 10 herein described have a lower setting on the front panel 14 and so the roll off of the power may be a percentage of the decrease described. To do this the command to the microprocessor 15 may be changed. For example, if the Iscaled is equal to or less than Vscaled then the preferred control is to put the desired voltage at one half or fifty percent, see FIG. 4 wherein the power roll off is the end of the curve for impedances of greater than one thousand and twenty four.

The feedback technique programmed into control to the microprocessor 15 is as follows: when the feedback technique programmed into the instruction is one, Econ 33, i.e. control voltage is adjusted until the Iscaled is made closer to Idesired. When the feedback technique programmed into the instruction is three, Econ 33 is adjusted so that the actual power is made closer to the desired power as set by the surgeon on the front panel 14. A word about the front panel 14 settings for power desired, the preferred embodiment in the Valleylab NS 2000 has numerical indicia that allow a fine adjustment upward or downward without being in watts or other power units. This is done on purpose to allow a finer gradation and to eliminate a preconceived notion of a particular wattage as adequate. Remember that the actual scale of the front panel 14 control knob 38 used to set the initiating power between about zero and fifteen watts.

When the feedback technique programmed into the instruction is two, Econ 33 is adjusted until Vscaled is made closer to the desired voltage programmed into the microprocessor 15 as per the impedance range being monitored, e.g. five hundred and twelve to one thousand twenty four and so on to infinity. With regard to the latter the high or low power range 41 set on the front panel 14 see FIG. 1 will control the feedback technique programmed into the instruction, as explained.

Figure 5:
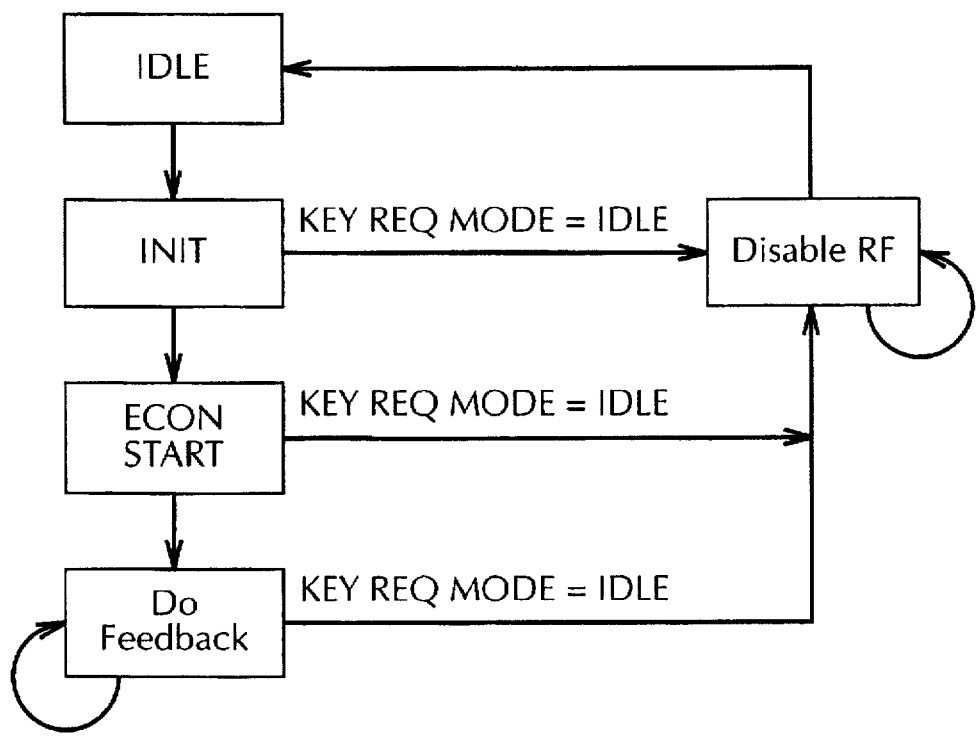
FIG. 5 is a schematic block diagram of an activation circuit in a microprocessor for feedback which is a part of the control system.
Figure 7:
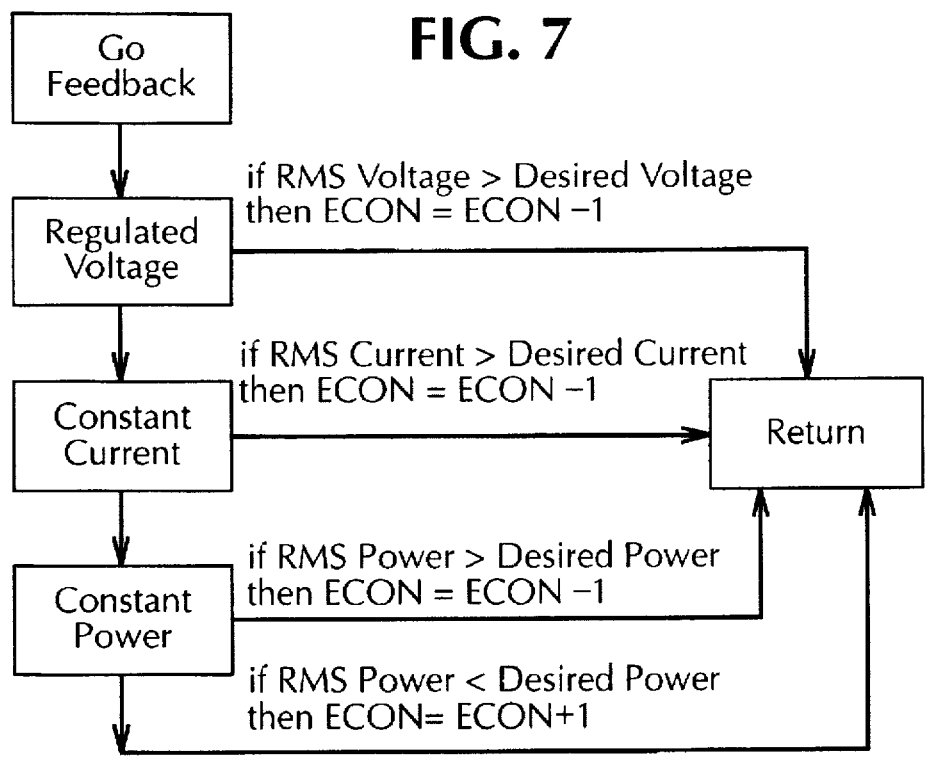
FIG. 7 is a schematic block diagram of the feedback technique programmed into a microprocessor wherein there is no feedback required of the control system.
Figure 6:
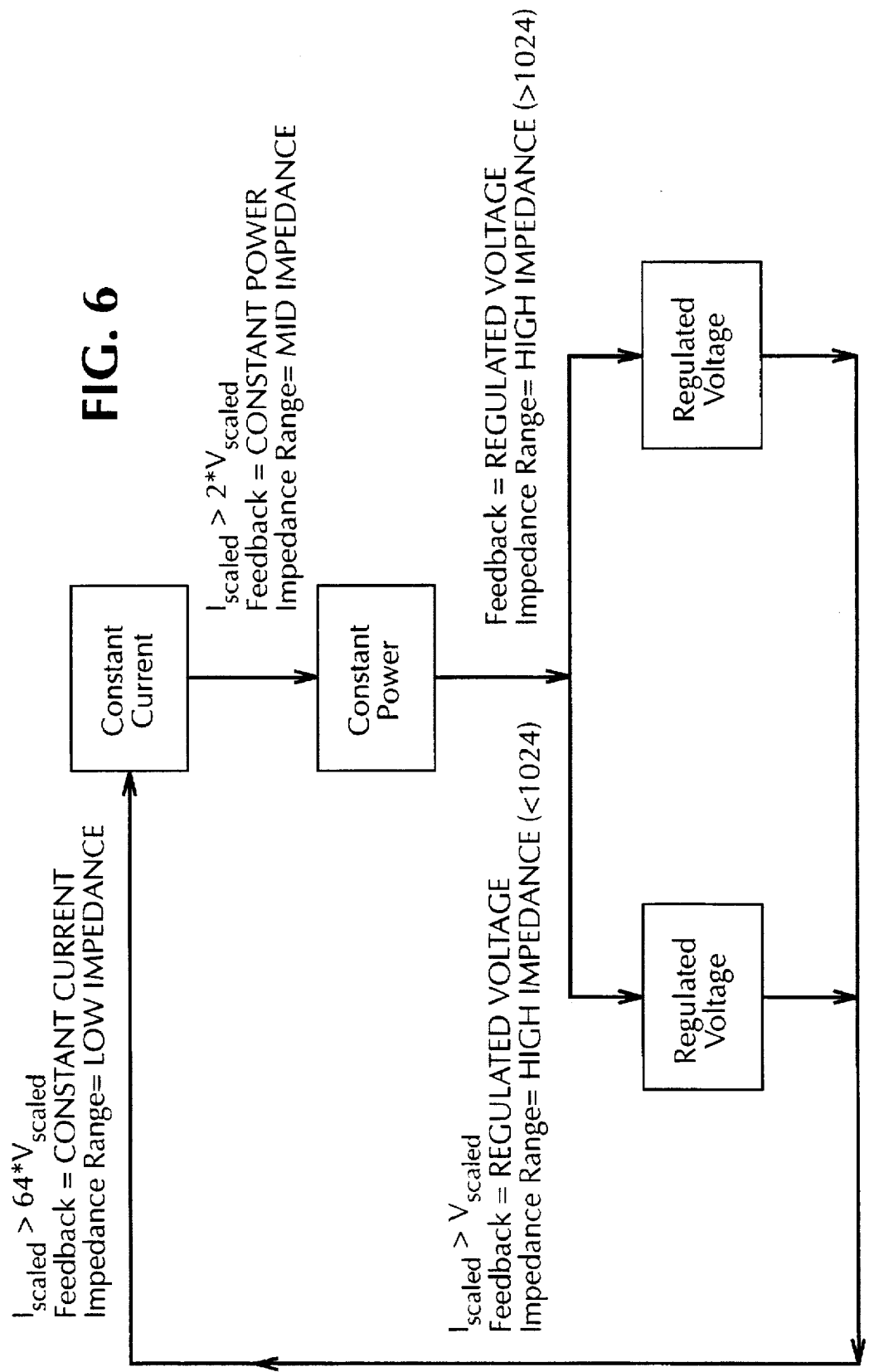
FIG. 6 is a schematic block diagram of a feedback technique programmed into a microprocessor which is a part of the control system when feedback is called for by the control system.

FIGS. 5, 6 and 7 are schematic block diagrams of the feedback technique programmed into the microprocessor followed by the microprocessor 15. Starting at the upper block designated idle in FIG. 5 the condition of the microprocessor 15 being on but inactive is shown. In the idle setting the microprocessor 15 has in its memory the settings from the front panel 14, i.e. high or low range 41 and amount of power at knob 38 and on display 37 as well as the ultimate on or off at 39. Immediately below the idle block is the initiate or disable functions associated with the foot switch 16 for keying the source of high frequency energy 13' by the surgeon. Below the block for initiation or disable is another block titled, "start Econ 33" which drives the source of high frequency energy 13' once the keying has taken place. The automatic operation according to the power curves follow.

Beneath the start block is the start Econ 33 block representative of the plus one minus one impetus for the source of high frequency energy 13' which produces the power curve either FIG. 3 or FIG. 4. The plus one minus one Econ 33 dithers the output roughly in accord with and instantaneously with respect to real time as described. Indicative of that is the next block labeled, "do feedback" which has programmed therewithin the calculations of the numbers that the control system 10 uses to generate the preferred power curve that will desiccate the neurological tissue and bodily fluids 12 without sticking to the bipolar forceps 11. The four considerations of the impedance analysis as described will be performed and the connection to the previous blocks as shown in FIG. 5 will complete the feedback technique programmed into the microprocessor as practiced by the microprocessor 15. While the feedback technique programmed into the microprocessor as instructions are explained as being 1, 2 or 3 those are entirely arbitrary numbers and can be anything the computer expert selects for the microprocessor 15.

A method for controlling the operation of neurosurgical bipolar electrodes 11 for application to the tissue and bodily fluids 12 of a patient has the steps of providing the source of high frequency energy 13', connecting bipolar electrodes 11 to the source of high frequency energy 13', providing contacting surfaces 25 on the bipolar electrodes 11, contacting the tissue and bodily fluids 12 with the contacting surfaces 25 of highly electrically conductive material with resistance per unit area substantially less than the impedance of the tissue and bodily fluids 12, having the tank network 22 in the source of high frequency energy 13', including capacitors and inductors tuned to the operating frequency of the source of high frequency energy 13' in the tank network 22, providing as output of the source of high frequency energy 13' the tank network 22, inductively attaching the first current transducer 17 to the connection between the source of high frequency energy 13' and one of the contact surfaces 25, responding with the first current transducer 17 to the instantaneously varying impedance of the load of the tissue and bodily fluids 12 at the particular instant of treatment of the tissue and bodily fluids 12, providing with the first current transducer 17 the measure 20 relative to the instantaneous values of the RMS current between the contact surfaces 25 and through the tissue and bodily fluids 12, responding to the RMS current applied through the tissue and bodily fluids 12 between the contact surfaces 25, inductively attaching the second current transducer 18 to the source of high frequency energy 13' to respond to the RMS current through the capacitor 23 applied across the contact surfaces 25, providing with the second current transducer 18 the signal 19 of the varying current changes due to the tissue impedance load on the source of high frequency energy 13' and changes in the output thereof due to variance in the radio frequency sourced energy, providing with the second current transducer 18 the signal 19 representative of the instantaneous value of RMS voltage across the tissue and bodily fluids 12 between the contact surfaces 25, providing with the second transducer 18 the signal 19 correlated to by a weighted value of the instantaneous value of RMS voltage, connecting a control for example Econ 33, to the source of high frequency energy 13' for initially regulating the RMS current applied through the tissue and bodily fluids 12 by the contacting surfaces, responding with the control Econ 33 to the impedance the tissue and bodily fluids 12 until the signal divided by the measure reaches a predetermined value, connecting the control Econ 33 for then regulating the RMS power applied to the tissue and bodily fluids 12 by the contacting surfaces 25 in accord with the impedance in the tissue and bodily fluid 12 until the signal 19 divided by the measure 20 reaches a predefined value, responding thereafter with the control Econ 33 to the signal 19 divided by the measure 20 so that the RMS voltage applied to the impedance of the tissue and bodily fluids 12 being treated between the contacting surfaces 25 is regulated while monitored until the signal 19 divided by the measure 20 of a prescribed value, the control Econ 33 connected for finally regulating the RMS voltage applied to the tissue and bodily fluids 12 by the contacting surfaces 25 in accord with the impedance in the tissue by changing the RMS voltage to a percentage of that applied to the tissue and bodily fluid 12 until the prescribed value is obtained so that the tissue and bodily fluids 12 being treated are moist but coagulated at the surface and not completely dry and carbonized or turned to eschar.

Alternatively the control system 10 for neurosurgical bipolar electrodes 11 for application by a surgeon to the tissue and bodily fluids 12 of a patient connects to the source of high frequency energy 13' and it regulates the RMS current, RMS power and RMS voltage applied through the tissue and bodily fluids 12 by the contacting surfaces 25 and responds to the impedance therethrough. The microprocessor 15 connects for receiving the instantaneous values of the measure and the signal in real time. The microprocessor 15, which operates in the binary system for receiving from the control and thereafter relating the measure to the signal, the microprocessor 15 having memory for the predetermined value and for assessing when the measure related to the signal is the predetermined value, the microprocessor 15 having memory for the predefined value and for assessing when the measure related to the signal is the predefined value, the microprocessor 15 having memory for the prescribed value and for assessing when the measure related to the signal is the prescribed value. The microprocessor 15 able to compare the measure relative to the signal to the predetermined value, the predefined value or the prescribed value in real time. The control Econ 33 connected for regulating the RMS power applied to the tissue and bodily fluids 12 by the contacting surfaces 25 in accord with the impedance in the tissue and bodily fluids 12 until the measure 20 relative to the signal 19 has reached the predefined value. The control thereafter responds to the measure 20 relative to the signal 19 so that the RMS voltage applied to the impedance of the tissue and bodily fluids 12 being treated between the contacting surfaces 25 is regulated while monitored until the measure 20 relative to the signal 19 has reached the prescribed value. The control Econ 33 connects for finally regulating the RMS voltage applied to the tissue and bodily fluids 12 by the contacting surfaces 25 in accord with the impedance in the tissue by changing the RMS voltage to a percentage of that applied to the tissue and bodily fluids 12 until the prescribed value is obtained so that the tissue and bodily fluids 12 being treated are moist but coagulated at the surface and not completely dry and carbonized or turned to eschar.

While a particular control system 10 for bipolar forceps 11 has been described, it is understood that the circuitry the microprocessor 15 and the operation are limited only by the claims.

What is claimed is:

1. A control system for neurosurgical bipolar electrodes for application by a surgeon to tissue and bodily fluids of a patient, the tissue and bodily fluids having a tissue impedance, the control system comprising:
   a source of high frequency energy having an output and an operating frequency;
   a tank network in the source of high frequency energy, the tank network having at least a tank capacitor and at least a tank inductor, the at least tank capacitor and the at least tank inductor tuned to the operating frequency of the source of high frequency energy, the tank network connected to the output of the source of high frequency energy;
   bipolar electrodes connected to the output of the source of high frequency energy;
   contact surfaces on the bipolar electrodes, the contact surfaces comprised of highly electrically conductive material with resistance per unit area substantially less than the tissue impedance;
   a first current transducer inductively coupled to the bipolar electrodes, the first current transducer responsive to the tissue impedance, the first current transducer providing a measure relative to a first current through the tissue and bodily fluids;
   a second current transducer attached to the source of high frequency energy to respond to a second current through a second capacitor applied across the contact surfaces, the second current transducer providing a signal of changes in the second current, the signal representative of a voltage across the tissue and bodily fluids between the contact surfaces;
   a control connected to the source of high frequency energy for initially regulating the first current applied through the tissue and bodily fluids by the contact surfaces and for responding to the tissue impedance until the signal divided by the measure is a predetermined value, the control connected for then regulating power applied to the tissue and bodily fluids by the contact surfaces until the signal divided by the measure is a predefined value, the control for thereafter responding to the signal divided by the measure so that the voltage across the tissue and bodily fluids being treated between the contact surfaces is regulated while monitored until the signal divided by the measure is a prescribed value, so that the tissue and bodily fluids being treated are moist but coagulated at the surface and not completely dry and carbonized.

2. The control system for neurosurgical bipolar electrodes of claim 1 wherein the control includes a microprocessor, the microprocessor for dividing the signal by the measure, the microprocessor having memory for the predetermined value, the predefined value and the prescribed value and the microprocessor able to compare the predetermined value, the predefined value and the prescribed value to the signal divided by the measure in real time.

3. The control system for neurosurgical bipolar electrodes of claim 2 wherein the control has feedback technique programmed into the microprocessor for maintaining the current substantially constant until the signal divided by the measure is the predetermined value of sixteen.

4. The control system for neurosurgical bipolar electrodes of claim 2 wherein the control has feedback technique programmed into the microprocessor for maintaining the power substantially constant until the signal divided by the measure is the predefined value of five hundred and twelve.

5. The control system for neurosurgical bipolar electrodes of claim 2 wherein the control has feedback technique programmed into the microprocessor for maintaining the voltage substantially regulated until the signal divided by the measure is the prescribed value of one thousand and twenty four.

6. The control system for neurosurgical bipolar electrodes of claim 2 wherein the control has feedback technique programmed into the microprocessor for maintaining the voltage at a percentage of its substantially regulated level after the signal divided by the measure is the prescribed value of one thousand and twenty four.

7. The control system for neurosurgical bipolar electrodes of claim 2 wherein the microprocessor calculates the signal and the measure then multiplies them to calculate power in real time.

8. The control system for neurosurgical bipolar electrodes of claim 1 wherein the source of high frequency energy has a surgeon power knob limiting the source of high frequency energy to a range of between about 1 and 70 watts of output.

9. The control system for neurosurgical bipolar electrodes of claim 1 wherein the contact surfaces are composed of a metal selected from the group consisting of a noble metal, nickel and alloys thereof selected for their electrically and thermally conductive characteristics.

10. The control system for neurosurgical bipolar electrodes of claim 1 wherein a switch is located between the source of high frequency energy and the bipolar electrodes for the surgeon to activate and make a connection therebetween.

11. The control system for neurosurgical bipolar electrodes of claim 2 wherein the control has feedback technique programmed into the microprocessor for maintaining the voltage at fifty percent of its substantially regulated level after the signal divided by the measure is the prescribed value of one thousand and twenty four.

12. A method for controlling a system for neurosurgical bipolar electrodes for application to tissue and bodily fluids of a patient, the tissue and bodily fluids having a tissue impedance, the method comprising the steps of:
   providing a source of high frequency energy having an output stage and an operating frequency;
   connecting bipolar electrodes to the source of high frequency energy, the bipolar electrodes having contact surfaces of highly electrically conductive material having resistance per unit area substantially less than the tissue impedance;
   contacting the tissue and bodily fluids with the contact surfaces;

connecting a tank network to the output stage of the source of high frequency energy, the tank network including at least a tank capacitor and at least a tank inductor, the at least tank capacitor and the at least tank inductor tuned to the operating frequency;

inductively coupling a first current transducer to the bipolar electrodes:

responding with the first current transducer to the tissue impedance at the particular instant of treatment of the tissue and bodily fluids;

providing with the first current transducer a measure relative to the instantaneous values of current through the tissue and bodily fluids;

inductively coupling a second current transducer to the source of high frequency energy to respond to current through a second capacitor applied across the contact surfaces;

generating a signal with the second current transducer, the signal generated in response to the tissue impedance;

the signal correlated to an instantaneous value of voltage between the contact surfaces;

connecting a control to the source of high frequency energy for initially regulating current applied through the tissue and bodily fluids by the contact surfaces;

responding with the control to the tissue impedance until the signal divided by the measure reaches a predetermined value;

connecting the control for then regulating power applied to the tissue and bodily fluids by the contact surfaces in accord with the tissue impedance until the signal divided by the measure reaches a predefined value;

responding thereafter with the control to the signal divided by the measure so that voltage between the contact surfaces is regulated while monitored until the signal divided by the measure is a prescribed value, so that the tissue and bodily fluids being treated are moist but coagulated at the surface and not completely dry and carbonized.

13. A control system for neurosurgical bipolar electrodes for application by a surgeon to tissue and bodily fluids of a patient, the tissue and bodily fluids having a tissue impedance, the control system comprising:

a source of high frequency energy having an output and an operating frequency;

a tank network in the source of high frequency energy, the tank network having at least a tank capacitor and at least a tank inductor, the at least tank capacitor and the at least tank inductor tuned to the operating frequency of the source of high frequency energy, the tank network as the output of the source of high frequency energy for generating an output power and an output voltage;

bipolar electrodes connected to the output of the source of high frequency energy;

contact surfaces on the bipolar electrodes, the contact surfaces comprised of highly electrically conductive material with resistance per unit area substantially less than the tissue impedance;

a first current transducer inductively coupled to the bipolar electrodes the first current transducer responsive to the tissue impedance, the first current transducer providing a measure relative to a first current through the tissue and bodily fluids;

a second current transducer attached to the source of high frequency energy to respond to a second current through a second capacitor applied across the contact surfaces, the second current transducer providing a signal of changes in the second current, the signal representative of the output voltage;

a control connected to the source of high frequency energy for regulating the first current, the output power and the output voltage and for responding to the tissue impedance, the control connected for receiving the measure and the signal in real time;

a microprocessor in the control, the microprocessor for receiving from the control and thereafter relating the measure to the signal, the microprocessor having memory for a predetermined value and for assessing when the signal divided by the measure equals the predetermined value, the microprocessor having memory for predefined value and for assessing when the signal divided by the measure equals the predefined value, the microprocessor having memory for a prescribed value and for assessing when the signal divided by the measure equals the prescribed value, and the control connected to the source of high frequency energy for regulating the first current applied to the tissue and bodily fluids by the contact surfaces in accord with the tissue impedance until the signal divided by the measure is the predetermined value, the control for thereafter responding to the signal divided by the measure so that the output power is regulated while monitored until the signal divided by the measure is the value, the control connected for finally regulating the output voltage by changing the output voltage to a percentage of that applied to the tissue and bodily fluid until the prescribed value is obtained so that the tissue and bodily fluids being treated are moist but coagulated at the surface and not completely dry and carbonized.

14. The control system for neurosurgical bipolar electrodes of claim 13 wherein the control has feedback technique programmed into the microprocessor for maintaining the voltage at fifty percent of its substantially regulated level after the signal divided by the measure is the prescribed value of one thousand and twenty four.

15. The control system for neurosurgical bipolar electrodes of claim 13 wherein the control has feedback technique programmed into the microprocessor for maintaining the voltage at one hundred percent of its substantially regulated level until the signal divided by the measure is the prescribed value of one thousand and twenty four.

* * * * *